(12) United States Patent
Duckett, III (10) Patent No.: US 12,396,621 B2
(45) Date of Patent: Aug. 26, 2025

(54) FRAME PROCESSING OF IMAGING SCOPE DATA FOR USER INTERFACE PRESENTATION

(71) Applicant: KARL STORZ Imaging, Inc., Goleta, CA (US)

(72) Inventor: George E. Duckett, III, Castaic, CA (US)

(73) Assignee: KARL STORZ Imaging, Inc., Goleta, CA (US)

( * ) Notice: Subject to any disclaimer, the term of this patent is extended or adjusted under 35 U.S.C. 154(b) by 901 days.

(21) Appl. No.: 17/644,322

(22) Filed: Dec. 14, 2021

(65) Prior Publication Data

US 2023/0181002 A1    Jun. 15, 2023

(51) Int. Cl.

| | |
|---|---|
| *A61B 1/00* | (2006.01) |
| *A61B 1/04* | (2006.01) |
| *A61B 1/06* | (2006.01) |
| *G06T 7/00* | (2017.01) |
| *G16H 30/20* | (2018.01) |
| *G16H 50/20* | (2018.01) |
| *H04N 5/262* | (2006.01) |
| *H04N 23/56* | (2023.01) |

(Continued)

(52) U.S. Cl.
CPC ........ *A61B 1/0004* (2022.02); *A61B 1/00043* (2013.01); *A61B 1/00045* (2013.01); *A61B 1/044* (2022.02); *A61B 1/0676* (2013.01); *G06T 7/0012* (2013.01); *G16H 30/20* (2018.01); *G16H 50/20* (2018.01); *H04N 5/2628* (2013.01); *H04N 23/56* (2023.01); *H04N 23/80* (2023.01); *A61B 1/000096* (2022.02); *G06N 3/08* (2013.01); *G06T 2207/10064* (2013.01); *G06T 2207/10068* (2013.01); *G06T 2207/20084* (2013.01); *G06T 2207/30096* (2013.01); *H04N 23/555* (2023.01)

(58) Field of Classification Search
None
See application file for complete search history.

(56) References Cited

U.S. PATENT DOCUMENTS

| | | |
|---|---|---|
| 6,663,559 B2 | 12/2003 | Hale |
| 7,052,455 B2 | 5/2006 | Hale |

(Continued)

FOREIGN PATENT DOCUMENTS

CN     109920518 A     6/2019

OTHER PUBLICATIONS

Fischer, Martin, Extended European Search Report, Apr. 11, 2023, pp. 1-7, European Patent Office, Munich.

*Primary Examiner* — Yi-Shan Yang
(74) *Attorney, Agent, or Firm* — Jason H. Vick; Amped IP LLC (57) ABSTRACT

Improved medical scope devices and systems are provided to with two imaging modes and user interface features based on the imaging modes. A medical scope has a shaft with a light emitter at the distal tip providing illumination light and an optical assembly including a wide-angle lens element. A processor controls a display to show an adjustable region of interest (ROI) smaller than a field of view of the image sensor. Responsive to designated conditions, a frame is selected for diagnostic image processing to determine whether a feature of interest (FOI) is present in the frame. Responsive to an FOI being present in the frame but outside the ROI, a notification is created on the electronic display.

26 Claims, 9 Drawing Sheets

(51) Int. Cl.
    *H04N 23/80*     (2023.01)
    *G06N 3/08*     (2023.01)
    *H04N 23/50*     (2023.01)

(56) References Cited

U.S. PATENT DOCUMENTS

| | | |
|---|---|---|
| 7,221,522 B2 | 5/2007 | Tesar |
| 8,758,234 B2 | 6/2014 | Hale |
| 8,771,177 B2 | 7/2014 | Hale |
| 8,814,782 B2 | 8/2014 | Hale |
| 8,870,758 B2 | 10/2014 | Dahmen |
| 9,182,577 B2 | 11/2015 | Hoeg |
| 9,392,930 B2 | 7/2016 | Lei |
| 9,408,527 B2 | 8/2016 | Hoeg |
| 9,615,772 B2 | 4/2017 | Hale |
| 9,986,169 B2 | 5/2018 | Morales |
| 10,092,169 B2 | 10/2018 | Hale |
| 10,600,510 B2 | 3/2020 | Mohr |
| 10,891,737 B2 * | 1/2021 | Saito .................. G06T 7/11 |
| 12,087,012 B2 * | 9/2024 | Dikhale .............. B25J 9/1694 |
| 2011/0301447 A1 | 12/2011 | Park |
| 2014/0133703 A1 | 5/2014 | Dogra |
| 2015/0002734 A1 * | 1/2015 | Lee .................. H04N 25/531 |
| | | 348/367 |
| 2016/0325680 A1 * | 11/2016 | Curtis ................ H04W 4/024 |
| 2019/0205623 A1 | 7/2019 | Wang |
| 2020/0069160 A1 | 3/2020 | Oosake |
| 2020/0120288 A1 * | 4/2020 | Kitano .............. A61B 1/00006 |
| 2020/0273581 A1 * | 8/2020 | Wolf .................. G16H 40/63 |
| 2021/0153722 A1 | 5/2021 | Karino |
| 2021/0204802 A1 | 7/2021 | Nir |

* cited by examiner

FRAME PROCESSING OF IMAGING SCOPE DATA FOR USER INTERFACE PRESENTATION

TECHNICAL FIELD OF THE INVENTION

The invention relates generally to the field of medical image capture and more specifically to endoscope designs for improving frame processing and user interface presentation.

BACKGROUND OF THE INVENTION

Endoscopes and other medical scopes often use fluorescing agents or autofluorescence to better examine tissue. A fluorescing agent such as a dye may be injected or otherwise administered to tissue. Subsequently, an excitation light is directed toward the tissue. Responsive to the excitation light, the fluorescing agent fluoresces (emits light, typically at a longer wavelength than the excitation light), allowing a sensor to detect this emission light. Image data is collected by the sensor and examining the collected images can indicate the concentration of fluorescing agent in the observed tissue.

Some existing endoscopes are able to switch between visible light imaging and FI imaging. However, when those modes are used together, the scopes suffer from a strobing effect in the visible imagery or require complicated techniques to recognize and overlay information from FI imaging onto a visible light imaging display. What is needed are devices and methods to provide improved endoscope solutions that enable improved user interfaces for endoscopic procedures.

SUMMARY OF THE INVENTION

It is an object of the invention to improve the user interface of dual mode endoscopes. It is another object of the invention to provide an endoscope and image processor to enable such an improved interface.

According to one aspect of the invention, imaging scope system is provided including a shaft including a distal tip with a light emitter providing illumination light and an optical assembly including a wide-angle lens element. An image sensor assembly includes an image sensor configured to receive at least a portion of light focused through the optical assembly and produce output signals. Image forming circuitry adapted to receive the output signals and produce an image signal communicating a series of image frames. A processor coupled to the image forming circuitry is configured to: condition the image signal for presentation on an electronic display, the presentation including an adjustable region of interest (ROI) smaller than a field of view of the image sensor and omitting image data outside the ROI; responsive to designated conditions, select a frame from the series for diagnostic image processing, and evaluate results of the diagnostic image processing to determine whether a feature of interest (FOI) is present in the frame; and responsive to an FOI being present in the frame but outside the ROI, create a notification on the electronic display.

According to some implementations of the first aspect, the processor is further configured to cause the light emitter to alter the illumination light from a first state to a second state during a time in which the selected frame is captured by the image sensor, and return to the first state following capture of the selected frame. The spectral content of the second state may be different than the spectral content of first state. The second state may include illumination light appropriate to stimulate fluorescence in properly prepared tissue. The second state may consist essentially of light from the spectral band spanning 350-450 nm. The second state may be of a higher intensity than the first state. The second state may have a wider field of illumination than that of the first state.

According to some implementations of the first aspect, the processor is further configured to cause the selected frame not to be displayed in the presentation, and instead replace it with imagery based on at least one frame prior to the selected frame.

According to some implementations of the first aspect, the notification indicates the relative direction from the ROI to the FOI.

According to some implementations of the first aspect, the diagnostic image processing includes an artificial intelligence (AI) algorithm for detecting cancerous or precancerous tumors or lesions. The AI algorithm may include a trained convolutional neural network (CNN).

According to some implementations of the first aspect, the designated conditions include the passage of a periodic time interval of at least 500 ms.

According to some implementations of the first aspect, the designated conditions include receiving a signal from a movement sensor on the imaging scope indicating that the imaging scope has moved more than a designated threshold.

According to some implementations of the first aspect, the designated conditions include a change in the content of the frames in the ROI above a designated threshold.

According to a second aspect of the invention, a method includes at a processor, receiving an image signal based on sensor data received from an image sensor of an imaging scope. The method includes conditioning the image signal for presentation on an electronic display, the presentation including an adjustable region of interest (ROI) smaller than a field of view of the image sensor and omitting image data outside the ROI. Responsive to designated conditions, the method selects a frame from the series for diagnostic image processing. The method includes performing diagnostic image processing and evaluating results of the diagnostic image processing to determine whether a feature of interest (FOI) is present in the frame. Responsive to an FOI being present in the frame but outside the ROI, the method includes causing a notification to be displayed on the electronic display.

According to some implementations of the second aspect, the method includes causing a light emitter on the imaging scope to alter the illumination light from a first state to a second state during a time in which the selected frame is captured by the image sensor, and return to the first state following capture of the selected frame. The spectral content of the second state may be different than the spectral content of first state. The second state may include illumination light appropriate to stimulate fluorescence in properly prepared tissue. The second state may consist substantially of light from the spectral band spanning 350-450 nm. The second state may be of higher intensity than the first state. The second state may have a wider field of illumination than that of the first state.

According to some implementations of the second aspect, the method may further include causing the selected frame not to be displayed in the presentation, and instead replacing it with imagery based on at least one frame prior to the selected frame.

According to some implementations of the second aspect, the notification may indicate the relative direction from the ROI to the FOI.

According to some implementations of the second aspect, the diagnostic image processing includes an artificial intelligence (AI) algorithm for detecting cancerous or precancerous tumors or lesions. The AI algorithm may include a trained convolutional neural network (CNN).

According to some implementations of the second aspect, the designated conditions include the passage of a regular periodic time interval of at least 500 ms.

According to some implementations of the second aspect, the designated conditions include receiving a signal from a movement sensor on the imaging scope indicating that the imaging scope has moved more than a designated threshold.

According to some implementations of the second aspect, wherein the designated conditions include a change in the content of the frames in the ROI above a designated threshold.

These and other features of the invention will be apparent from the following description of the preferred embodiments, considered along with the accompanying drawings.

BRIEF DESCRIPTION OF THE DRAWINGS

The present invention will become more fully understood from the detailed description given herein and the accompanying drawings which are given by way of illustration only, and thus are not limitative of the present invention, and wherein.

DETAILED DESCRIPTION OF EXAMPLE EMBODIMENTS

As used herein, first elements (e.g., sensors and lenses) that are "optically arranged" in relation to other elements, refers to the first elements' position along a common optical path that includes first and other elements. For example, a lens group optically arranged between an image sensor and an objective, means that the lens group occupies a portion of the optical path that light travels (e.g., from the objective to the image sensor) for capturing images or video.

Because digital cameras, visible light imaging sensors, FI sensors and related circuitry for signal capture and processing are well-known, the present description will be directed in particular to elements forming part of, or cooperating more directly with, a method and apparatus in accordance with the invention. Elements not specifically shown or described herein are selected from those known in the art. Certain aspects of the embodiments to be described are provided in software. Given the system as shown and described according to the invention in the following materials, software not specifically shown, described or suggested herein that is useful for implementation of the invention is conventional and within the ordinary skill in such arts.

Figure 1:
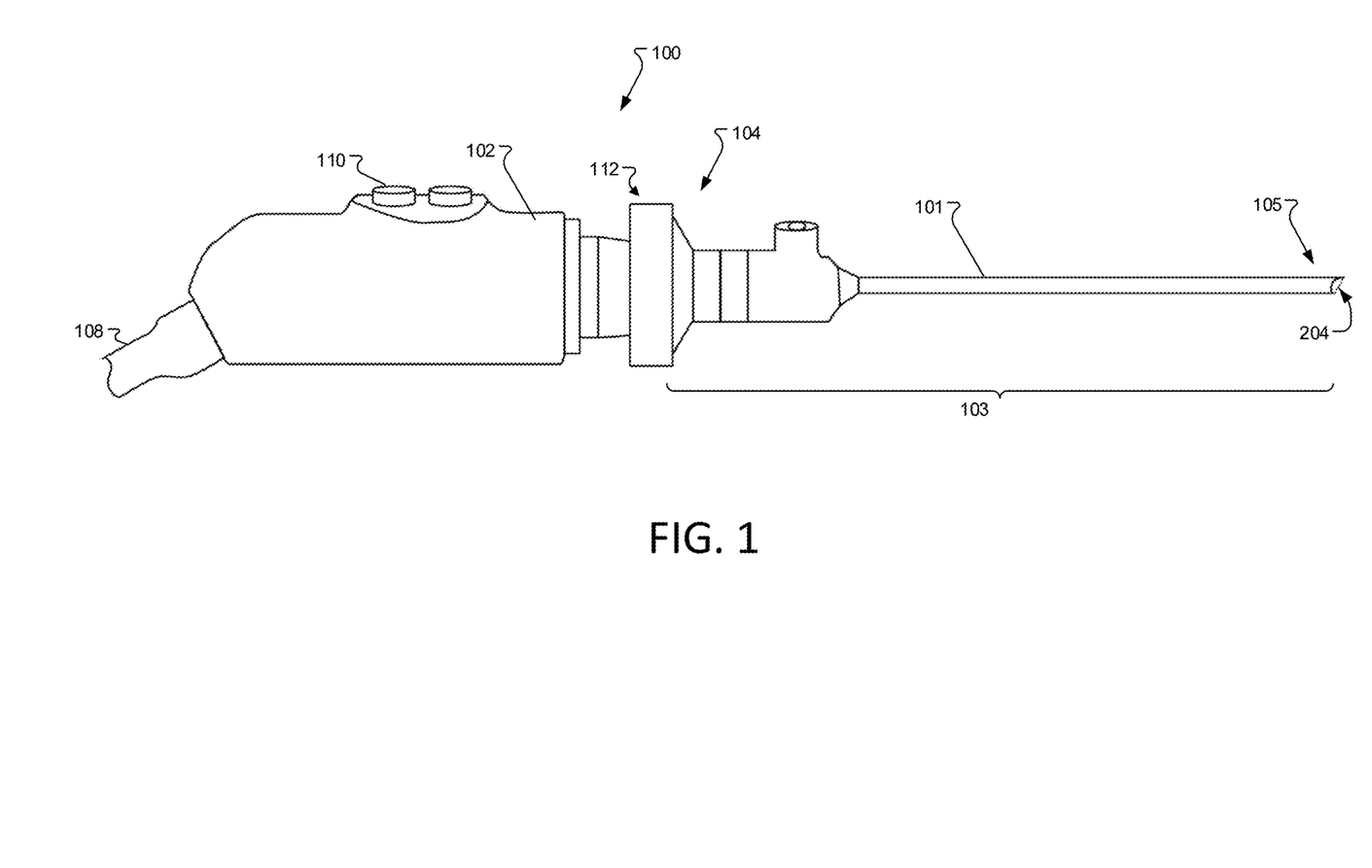
FIG. 1 shows a perspective view of a medical scope having a rigid shaft according to some embodiments.

Referring to FIG. 1, depicted is a perspective view of a medical scope 100 according to one aspect of the present invention and generally includes a scope element 103 including an elongated shaft 101, the scope element being connected to a camera head 102. In this embodiment, scope 103 can be detachably connected to the camera head 102 by any means known in the art, such as a bayonet connector 112, or maybe the elements may be parts of a single instrument 100. In other embodiments, the camera head and scope shaft are merged into a single assembly. Shaft 101 extends from a proximal end shown generally at reference numeral 104 connected to camera head 102 to a distal end generally indicated at reference numeral 105. An objective lens 204, often a wide-angle lens, is located at the distal end 105 and may be positioned behind a viewing window. The rigid, elongated shaft 101 generally includes a relay lens system, such as a series of coupled rod lenses, to transmit an image collected by the objective lens 204 to the proximal 104 portion of the scope 103. The image is then received by the camera head 102. The shown shaft 101 is a rigid implementation, but flexible-shaft implementations are also possible (FIG. 2).

While this embodiment includes the image sensor in camera head 102, other embodiments may include the image sensors and associated optics in the distal end 105.

Camera head 102 receives electrical operating power through a cable 108 which extends from a proximal end of camera head 102 in this example instrument. This power may be used to operate one or more light sources or, in some embodiments, such as those with distally placed image sensors, other electronic elements mounted within distal portion 105, including one or more electronic image sensors. Also, data signals from such an imaging device may be communicated through appropriate conduits within shaft 101, when image sensors are distally placed, and handle 102 to cable 108. These data signals may be communicated through cable 108 to processing equipment (not shown) which processes the image data and drives one or more video monitors to display the images collected by the instrument 100. Those familiar with endoscopes and borescopes will appreciate that instrument 100 includes a number of additional features such as controls 110 for controlling the operation of the instrument. Although data transmission relating to the image sensors will be described further below, the general operation and control of medical scope 100 will not be described further herein in order to avoid obscuring the present invention in unnecessary detail.

Figure 2:
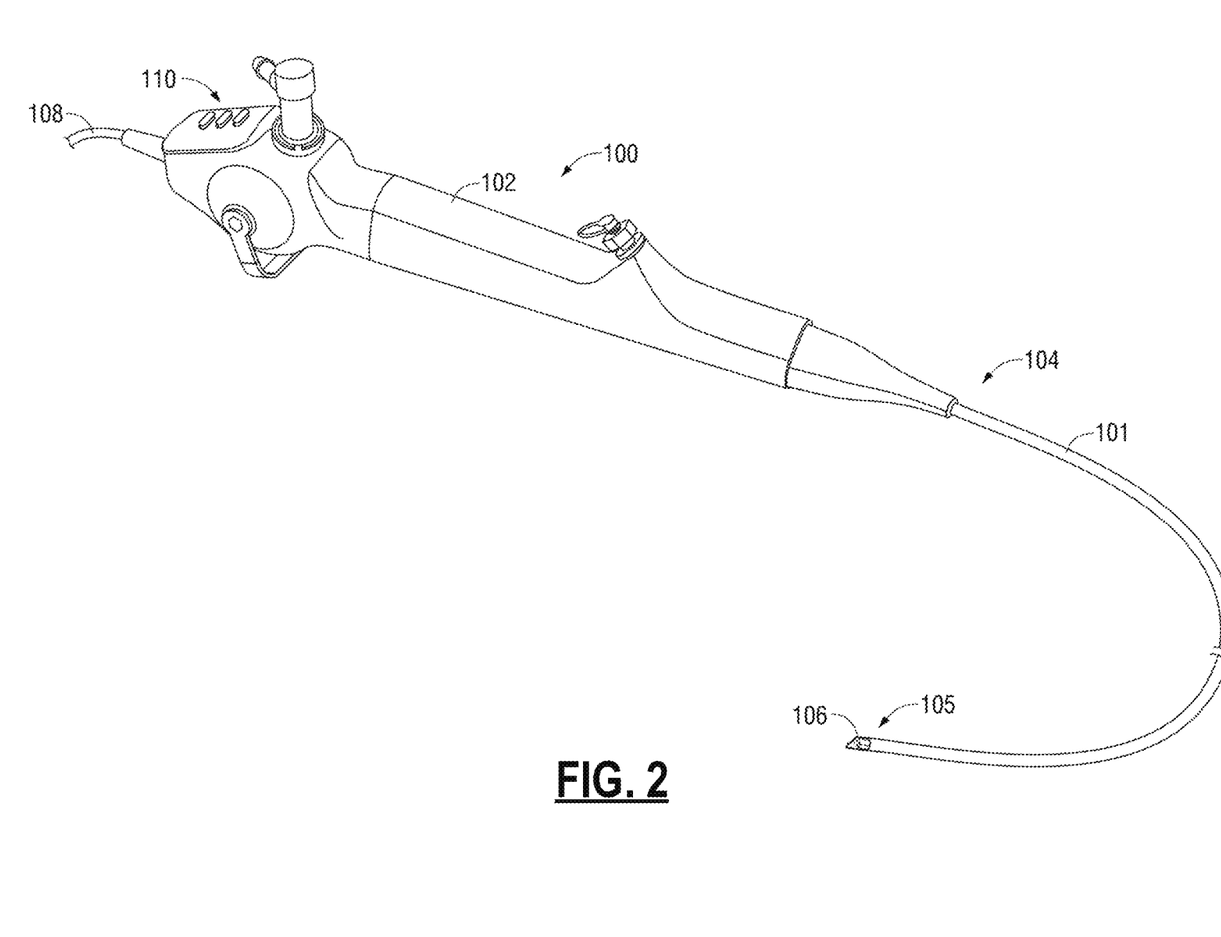
FIG. 2 shows a perspective view of a medical scope having a flexible shaft according to other embodiments.

Referring to FIG. 2, depicted is a perspective view of an optical instrument 100 according to another aspect of the present invention includes an elongated shaft 101 and a handle 102. Shaft 101 is a flexible shaft and extends from a proximal end shown generally at reference numeral 104 connected to handle 102 to a distal end generally indicated at reference numeral 105. The image sensors according to this embodiment are located in a distal end portion 106 of shaft 101.

Instrument 100 receives electrical operating power through a cable 108 which extends from a proximal end of handle 102 in this example instrument. This power may be used to operate one or more light sources and other electronic elements mounted within distal end portion 106, including one or more electronic image sensors. Also, data signals from such an imaging device may be communicated through appropriate conduits within shaft 101 and handle 102 to cable 108. These data signals may be communicated through cable 108 to processing equipment (not shown) which processes the image data and drives one or more video monitors to display the images collected at distal end 105 of instrument 100. Those familiar with endoscopes and borescopes will appreciate that instrument 100 includes a number of additional features such as controls 110 for controlling the operation of the instrument.

Figure 3:
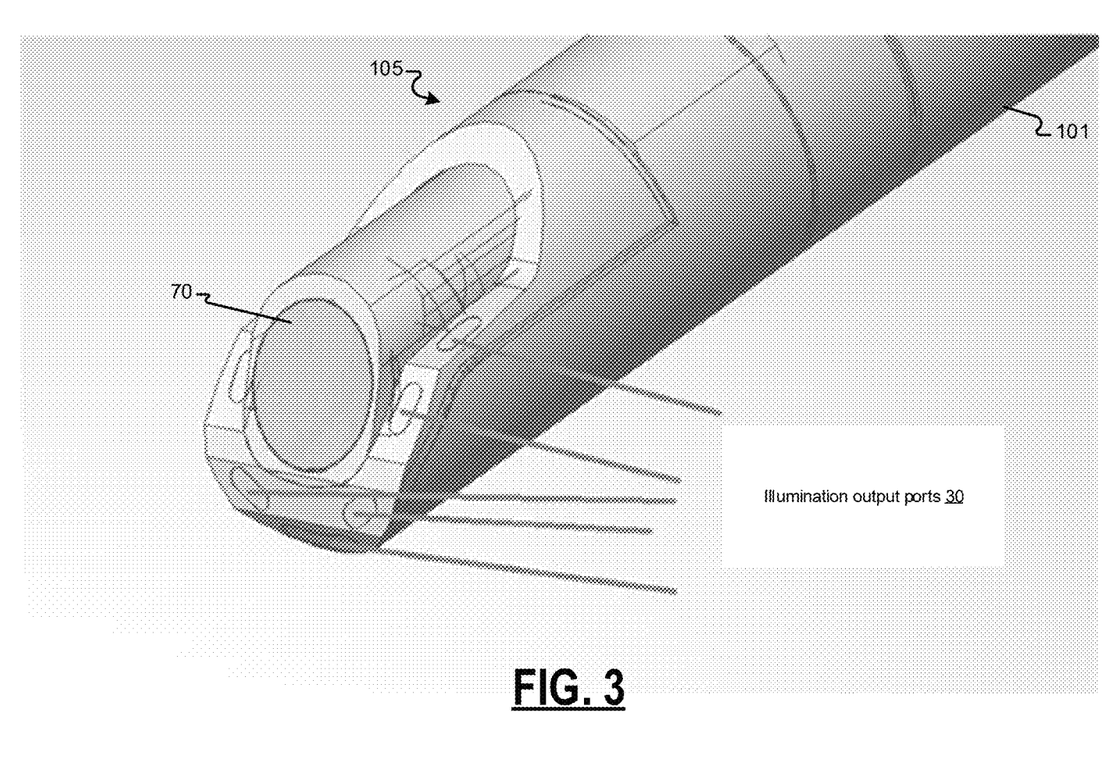
FIG. 3 shows a perspective view of a distal tip of a wide-angle endoscope according to some embodiments.

FIG. 3 shows a perspective view of a distal tip 105 of a wide-angle endoscope according to some embodiments. Distal tip 105 is positioned at the distal end of shaft 101, which may be a rigid shaft like that depicted in FIG. 1, or a flexible shaft like that of FIG. 2. Distal tip 105 includes a viewing window 70 behind which is positioned a wide-angle lens. A plurality of illumination output ports 30 are positioned along a distal surface of distal tip 105. In this embodiment, illumination output ports 30 are provided at both sides of viewing window 70, and positioned at various angles to provide a uniform illumination light along the viewing area of viewing window 70. As further described below, illumination output ports 30 may be individually controlled so as to vary the illumination light in different modes.

Figure 4:
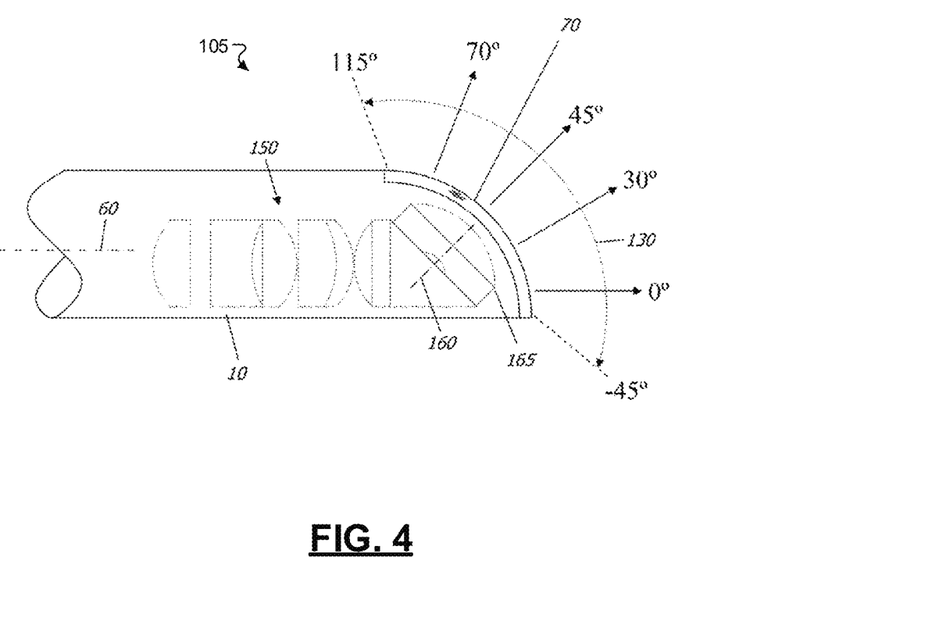
FIG. 4 shows a cross section of a distal tip of a wide-angle endoscope showing a lens system according to some embodiments.

FIG. 4 shows a cross section of a distal tip 105 of a wide-angle endoscope showing a lens system according to some embodiments. The depicted distal tip 105 has longitudinal axis 60, viewing window 70, and an optical assembly including a wide-angle lens system 165 with optical center 160 and a transmission system 150.

Figure 5:
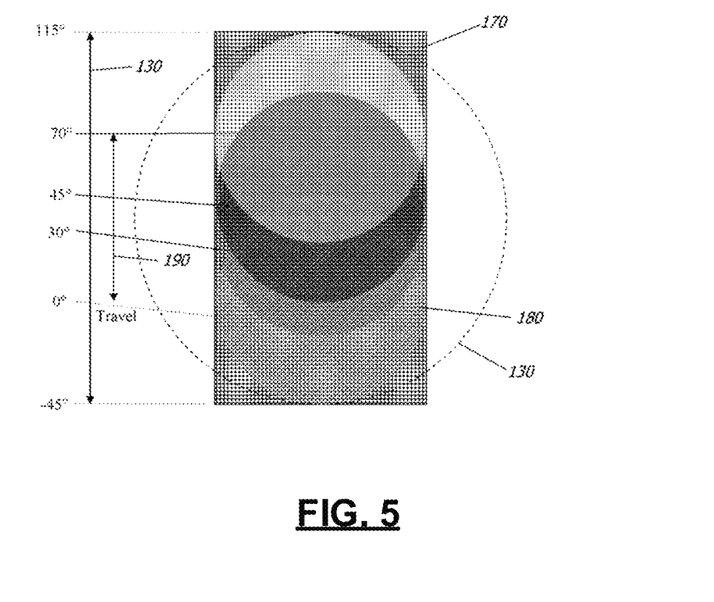
FIG. 5 is a diagram depicting an image sensor of the same endoscope relative to the endoscopic field of view.

FIG. 5 is a diagram depicting an image sensor of the same endoscope relative to the endoscopic field of view. As shown in FIG. 5, in some versions, the region of interest and viewing angle may be changed by a selection corresponding to a sub-set of pixels available from the image sensor.

Referring to FIG. 4 and FIG. 5, the optical center 160 is angularly offset from the longitudinal axis 60 of the endoscope 100 and covers a viewing range 130 of 160 degrees from −45 to +115 degrees relative to the longitudinal axis. From this configuration, the wide-angle lens system 165 simultaneously gathers an endoscopic image field 130 that spans the longitudinal axis and an angle greater than ninety degrees to the longitudinal axis. As a result, the simultaneous image field gathered by the endoscope provides both forward and retrograde imaging. Providing a variable view endoscope that spans this range is beneficial because it enables a user to view objects that reside in front of the endoscope and behind the standard fields of view for endoscopes. This improves the ability of a user to safely operate and handle the device in the body cavity. Further by incorporating a wide-angle lens with an optical center that is angularly offset relative to the longitudinal axis, the endoscope can more accurately mimic the viewing capabilities and function of a fixed angle endoscope.

The image field gathered by wide angle lens system 165 is conveyed to transmission system 150, which in turn conveys the wide-angle field of view to an image sensor surface area 170 that includes image surface area 170 formed by a plurality of pixels that gather light images and convert the images to output signals. The image surface area 170 is preferably rectangularly shaped with a longitudinal dimension that is greater than its lateral dimension, but can also be a variety of different shapes, such as square, circular or oval. Also, it is preferable that the image surface area 170 has an HD aspect ratio of 16:9. Since a wide-angle lens system can provide uneven information distribution, without correction an HD image sensor enables the crowded information regions to be captured and displayed on a monitor. As shown in FIG. 4, image surface area 170 partially captures field 130. It is preferable that the longitudinal dimension of image surface area 170 substantially correspond to the entire longitudinal dimension of field 130. This enables the endoscopic system to provide the user with an image or a range of regions of interest that span the field of view of the endoscope. However, image surface area 170 only captures a portion of the lateral dimension of field 130. Further, by limiting the lateral dimension of the sensor, the cross-sectional area of the endoscope can be more efficiently used. For instance, the lateral dimension of the wide-angle lens can be reduced and consequently reduce the overall size of the endoscope. Also, the cross-sectional area outside the area required for the sensor can be used to carry a fiber optic illumination system.

FIG. 5 also depicts specific regions of interest (ROIs) at 0, 30, 45 and 70 degrees which can be selected by a user over a designated range 190. A region of interest is an image area formed on the image surface area that is a subset of the overall field of view captured by the sensor. The center of the area of the ROI corresponds to a selected viewing angle chosen by a user, in this case a longitudinal viewing angle, but other offset directions may be used. The overall area of the ROI can correspond to the field of view typically provided by a fixed angled endoscope. Alternatively, the overall area of the ROI can be chosen to provide a minimal distortion variation across the overall area. Still further, the overall area of the ROI can be chosen such that the field encompassed by a viewing angle at least partially overlaps with an adjacent standard viewing angle, such as 30 and 45 degrees. ROIs that are sized to overlap with adjacent viewing angles assist a user in maintaining orientation in the event that a viewing angle is changed.

Because digital cameras and scopes employing imaging devices and related circuitry for signal capture, processing, correction, and exposure control are well-known, the present description will be directed in particular to elements forming part of, or cooperating more directly with, methods, and apparatus and program products in accordance with example embodiments of the invention. Elements not specifically shown or described herein are selected from those known in the art.

Figure 6:
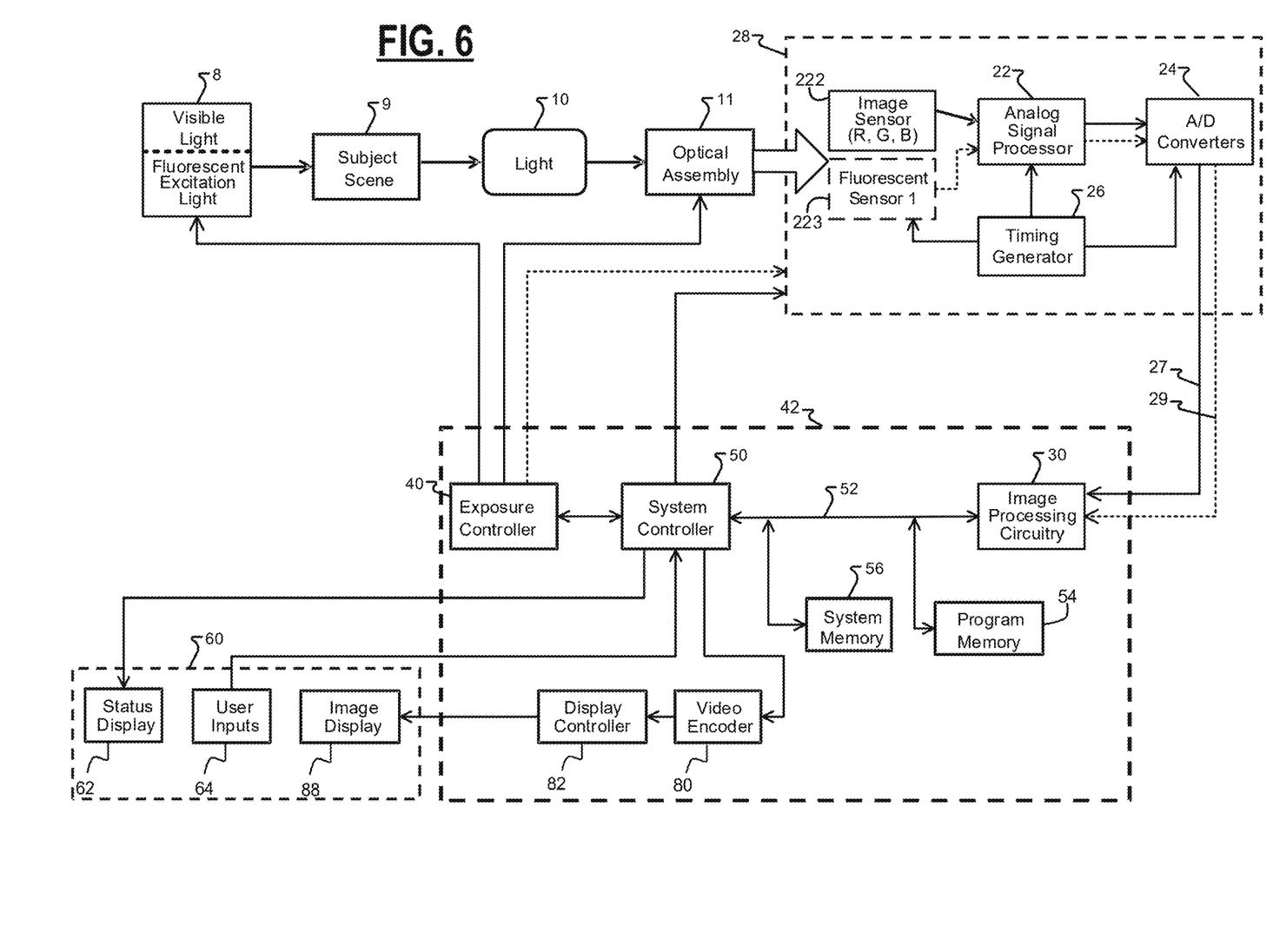
FIG. 6 is a hardware block diagram of system including an example image capture device according to an example embodiment.

FIG. 6 shows a block diagram of system including an image capture device and an endoscope device having an improved correction of chromatic aberration as described above. The invention is applicable to more than one type of device enabled for image capture, such as FI-capable endoscopes, other FI medical imaging devices. The preferred version is an imaging scope system, such as an endoscope.

As shown in the diagram of an endoscope device system, a light source 8 illuminates subject scene 9 with visible light and/or fluorescent excitation light, which may be outside the visible spectrum in the ultra-violet range or the infra-red/near infrared range, or both. Light source 8 may include a single light emitting element configured to provide light throughout the desired spectrum, or one or more visible light emitting elements and one or more fluorescent excitation light emitting elements. Further, light source 8 may include fiber optics passing through the body of the scope, or other light emitting arrangements such as LEDs or laser diodes positioned at or near the front of the scope.

As shown in the drawing, light 10 reflected from (or, alternatively, as in the case of fluorescence, excitation light 8 absorbed and subsequently emitted by) the subject scene is collected by an optical assembly 11, where the light is focused to form an image at a solid-state image sensor(s) 222 and/or fluoresced light sensor(s) 223.

Optical assembly 11 includes an optical relay system constructed according to the techniques provided herein. An additional lens group may be included at the camera head, as discussed with respect to FIG. 2. As discussed above, portions of the optical assembly may be embodied in a camera head or other first optical device, while other portions are in an endoscope or other scope device, or the optical assembly 11 may be contained in a single imaging device. Image sensor 222 (which may include separate R, G, and B sensor arrays) and fluoresced light sensor 223 convert the incident visible and invisible light to an electrical signal by integrating charge for each picture element (pixel). It is noted that fluoresced light sensor 223 is shown as an optional dotted box because embodiments may use the RGB image sensor 222 to detect only white light images or to also detect fluoresced light (e.g., NIR, ICG, FI). The latter scheme may be used when the fluoresced light is in a spectrum detectable by image sensor 222 that is in or near the visible light spectrum typically detected by a RGB sensor arrays.

Of course, alternate implementations of the present inventive relay lens systems are possible. For example, optical assembly 11 may include a dichroic beam splitting element and may direct one band of the spectra to one sensor for visual imaging and another band to another sensor for fluorescence imaging. As the present invention enables a scope side solution to the problems associated with chromatic aberration in relay systems, the camera head image sensor assembly 28 need not be adjusted to assure both visible and FI images are in focus.

The image sensor 222 and fluoresced light sensor 223 may be active pixel complementary metal oxide semiconductor sensors (CMOS APS) or charge-coupled devices (CCD).

The total amount of light 10 reaching the image sensor 222 and/or fluoresced light sensor 223 is regulated by the light source 8 intensity and the optical assembly 11 aperture. An exposure controller 40 responds to the amount of light available in the scene given the intensity and spatial distribution of digitized signals corresponding to the intensity and spatial distribution of the light focused on image sensor 222 and fluoresced light sensor 223.

Exposure controller 40 also controls the emission of fluorescent excitation light from light source 8, and may control the visible and fluorescent light emitting elements to be on at the same time, or to alternate to allow fluoresced light frames to be captured in the absence of visible light if such is required by the fluorescent imaging scheme employed. Exposure controller 40 may also control the optical assembly 11 aperture, and indirectly, the time for which the image sensor 222 and fluoresced light sensor 223 integrate charge. The control connection from exposure controller 40 to timing generator 26 is shown as a dotted line because the control is typically indirect.

Typically, exposure controller 40 has a different timing and exposure scheme for each of sensors 222 and 223. Due to the different types of sensed data, the exposure controller 40 may control the integration time of the sensors 222 and 223 by integrating sensor 222 up to the maximum allowed within a fixed 60 Hz or 50 Hz frame rate (standard frame rates for USA versus European video, respectively), while the fluoresced light sensor 223 may be controlled to vary its integration time from a small fraction of sensor 222 frame time to many multiples of sensor 222 frame time. The frame rate of sensor 222 will typically govern the synchronization process such that images frames based on sensor 223 are repeated or interpolated to synchronize in time with the 50 or 60 fps rate of sensor 222.

Analog signals from the image sensor 222 and fluoresced light sensor 223 are processed by analog signal processor 22 and applied to analog-to-digital (A/D) converter 24 for digitizing the analog sensor signals. The digitized signals each representing streams of images or image representations based on the data, are fed to image processor 30 as image signal 27, and first fluorescent light signal 29. For versions in which the image sensor 222 also functions to detect the fluoresced light, fluoresced light data is included in the image signal 27, typically in one or more of the three color channels.

Image processing circuitry 30 includes circuitry performing digital image processing functions to process and filter the received images as is known in the art. Image processing circuitry may include separate, parallel pipelines for processing the visible light image data and the FI image data separately. Such circuitry is known in the art and will not be further described here.

Image processing circuitry 30 may provide algorithms, known in the art, for combining visible light imagery with FI imagery in a combined image display, and further highlighting or emphasizing the FI imagery for easily distinguishing the presence of fluorescing features in the image.

Timing generator 26 produces various clocking signals to select rows and pixels and synchronizes the operation of image sensor 222 and fluorescent sensor 223, analog signal processor 22, and A/D converter 24. Image sensor assembly 28 includes the image sensor 222 and fluorescent sensor 223, adjustment control 20, the analog signal processor 22, the A/D converter 24, and the timing generator 26. The functional elements of the image sensor assembly 28 can be fabricated as a single integrated circuit as is commonly done with CMOS image sensors or they can be separately fabricated integrated circuits.

The system controller 50 controls the overall operation of the image capture device based on a software program stored in program memory 54. This memory can also be used to store user setting selections and other data to be preserved when the camera is turned off.

System controller 50 controls the sequence of data capture by directing exposure controller 40 to set the light source 8 intensity, the optical assembly 11 aperture, and controlling various filters in optical assembly 11 and timing that may be necessary to obtain image streams based on the visible light and fluoresced light. In some versions, optical assembly 11 includes an optical filter configured to attenuate excitation light and transmit the fluoresced light. A data bus 52 includes a pathway for address, data, and control signals.

Processed image data are continuously sent to video encoder 80 to produce a video signal. This signal is processed by display controller 82 and presented on image display 88. This display is typically a liquid crystal display backlit with light-emitting diodes (LED LCD), although other types of displays are used as well. The processed image data can also be stored in system memory 56 or other internal or external memory device.

The user interface 60, including all or any combination of image display 88, user inputs 64, and status display 62, is controlled by a combination of software programs executed on system controller 50. User inputs typically include some combination of typing keyboards, computer pointing devices, buttons, rocker switches, joysticks, rotary dials, or touch screens. The system controller 50 manages the graphical user interface (GUI) presented on one or more of the displays (e.g. on image display 88).

In particular, the system controller 50 will typically have a mode toggle user input (typically through a button on the endoscope or camera head itself, but possibly through a GUI interface), and in response transmit commands to adjust image processing circuitry 30 based on predetermined setting stored in system memory. Such settings may include different settings for different models of scopes that may be attached to a camera head or other imaging device containing image sensor assembly 28.

Image processing circuitry 30 is one of three programmable logic devices, processors, or controllers in this embodiment, in addition to a system controller 50 and the exposure controller 40. Image processing circuitry 30, controller 50, exposure controller 40, system and program memories 56 and 54, video encoder 80 and display controller 82 may be housed within camera control unit (CCU) 42.

CCU 42 may be responsible for powering and controlling light source 8, image sensor assembly 28, and/or optical assembly 11. In some versions, a separate front end camera module may perform some of the image processing functions of image processing circuitry 30.

Figure 7:
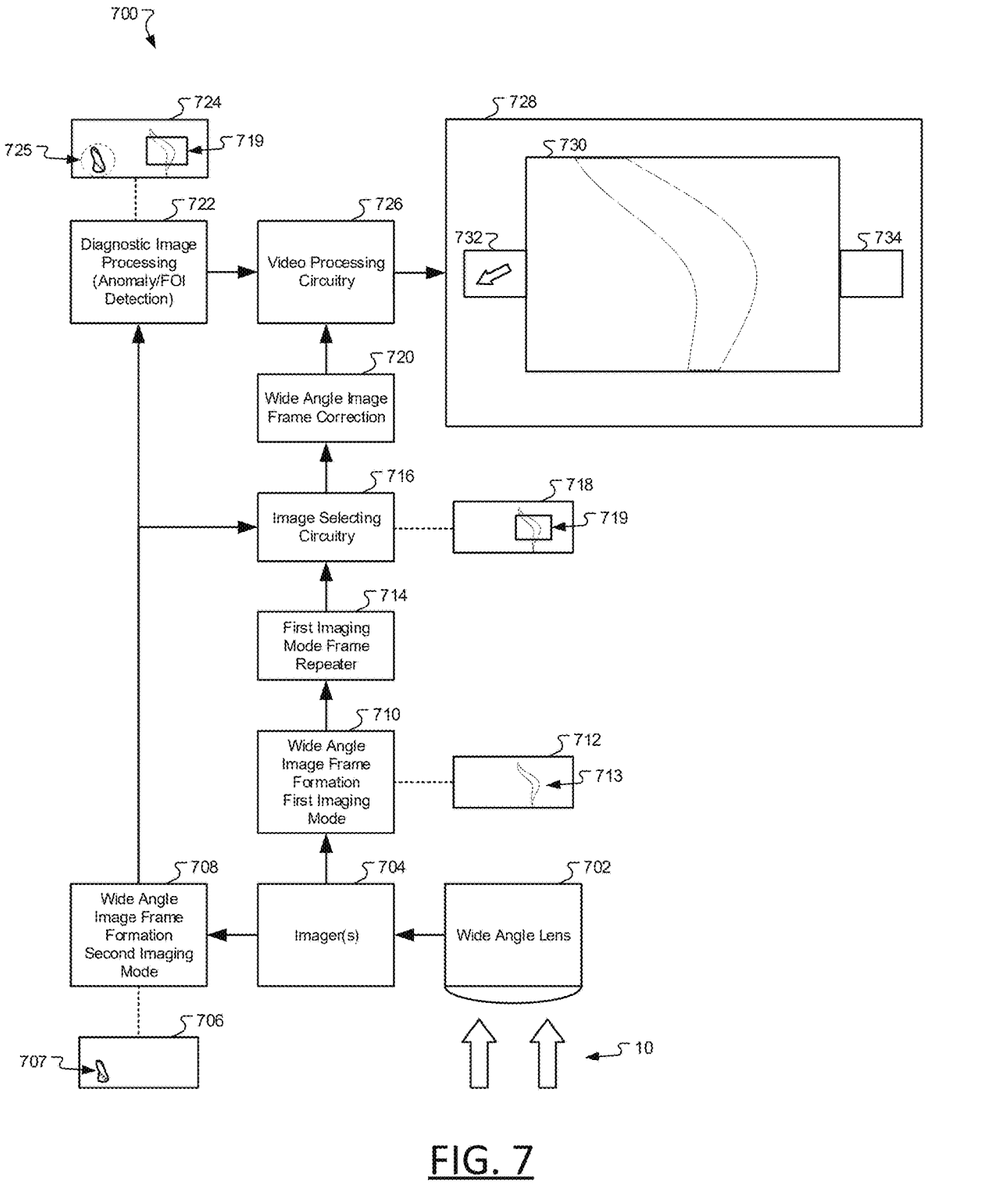
FIG. 7 shows a functional flow diagram of a process for operating an imaging scope system according some embodiments.

FIG. 7 shows a flow diagram 700 of a process for operating an imaging scope system according to some embodiments. The illustrated process is suitable for use with the imaging scope system described herein and variations thereof and is performed under control of a processor such as CCU 42. The process starts, as depicted toward the bottom of the flow diagram 700, as image light 10 is input to a wide-angle lens 702 and associated transmission system. The image light is directed to one or more imagers 704 of an image sensor assembly. The image sensor assembly includes an image sensor configured to receive at least a portion of light focused through the optical assembly and produce output signals, and image forming circuitry adapted to receive the output signals and produce an image signal communicating a series of image frames as described above with respect to the example embodiment of FIG. 6.

A processor such as CCU 42 is connected to the image forming circuitry and configured to receive and process image frames in a first mode and a second mode. As shown at block 710, the first mode includes forming image frames in a wide-angle image frame format which preferably includes a complete wide-angle view from the image sensor surface area 170 (FIG. 5). At block 714, a frame repeater is employed in some embodiments to reproduce frames for presentation to accommodate the second imaging mode, as further described below. The frame repeated may include DSP software functionality, digital logic, programmable digital logic, or some combination thereof embodied in circuitry such as image processing circuitry 30 (FIG. 6).

As shown at block 708, the second imaging mode includes wide angle image frame formation based on image frame data received from imagers at block 704. The second imaging mode is entered responsive to designated conditions, which may be a point in a periodic cycle or other designated conditions as further described below. In the second imaging mode, the processor selects a frame from the series for diagnostic image processing and performs diagnostic image processing as shown at block 722. The diagnostic image processing may include detecting an anomaly or other feature of interest (FOI) such as the anomaly 707 shown in image frame 706 captured in the second imaging mode. The process includes evaluating results of the diagnostic image processing to determine whether a feature of interest (FOI) is present in the frame as shown by the circled anomaly 725 in image frame 724 produced as an output to diagnostic image processing at block 722.

In various embodiments, the processor causes the light emitter to alter the illumination light in various ways from a first state to a second state during a time in which the selected frame is captured by the image sensor, and return to the first state following capture of the selected frame. In some embodiments, the spectral content of the second state is different than the spectral content of first state. In some embodiments, the second state includes illumination light appropriate to stimulate fluorescence in properly prepared tissue. For example, the second state may consist substantially of light from the spectral band spanning 350-450 nm, while the first state is white light or visible light. In some embodiments, second state is of higher intensity than the first state. In some embodiments, the second state has a wider field of illumination than that of the first state. For example, in one embodiment illumination output ports 30 (FIG. 3) are adjusted to increase the light intensity from the output ports that illuminate the imaging area toward the longitudinal ends of the image sensor surface area 170 (FIG. 5).

As shown at block 716, image selecting circuitry may be used to select between image frames from the first imaging mode or repeated frames produced by the frame repeater 714 and image frame formation block 710. The image selecting circuitry at block 716 is also employed in the first imaging mode to select an adjustable region of interest (ROI) smaller than a field of view of the image sensor and omitting image data outside the ROI. The image frame diagram shown at block 718 represents an original wide angle image frame captured in the first imaging mode, with a ROI 719 selected by the image selecting circuitry for display.

As shown at block 720, wide angle image correction may be performed to correct for distortion in the selected image.

Then at block 726, the process includes conditioning the image signal for presentation on an electronic display 728, both for repeated frames produced by first imaging mode frame repeater 714 and frames produced in the first imaging mode. The presentation represented at display area 730 of electronic display 728 includes displaying the ROI 719 and omitting image data outside the ROI. Preferably the ROI is adjustable by the user for panning along both axis and zooming in and out. Responsive to an FOI being present in the frame captured in the second imaging mode, but outside the ROI, such as the depicted anomaly 725 shown at a location outside ROI 719, the process creates a notification 732 on the electronic display. The notification preferably indicates the relative direction from ROI 719 to the FOI 725, as depicted by the displayed arrow in notification 732. Another notification area 734 is shown toward the opposite side of display 728 which is employed in this embodiment to indicate a relative direction toward an FOI if an FOI is detected in the relative position toward the right of ROI 719. As depicted, the notification may include a relative direction based on the offset on both the horizontal and vertical axis.

Because the second imaging mode may include different illumination from the first imaging mode, if image frames from both modes were displayed in the video stream in display area 730, a flashing or strobing effect might deleteriously affect the users experience in viewing the scope imagery. Therefore, in some embodiments the processor is configured to cause the selected frame not to be displayed in the presentation, and instead replace it with imagery created by the first imaging mode frame repeater at block 714 based on at least one frame prior to the selected frame. Further, the first imaging mode frame repeater may also create additional frames to compensate for visible effects resulting from the illumination changing states prior to and subsequent to the frame (706) employed for diagnostic image processing in the second imaging mode, as further described below.

Figure 8:
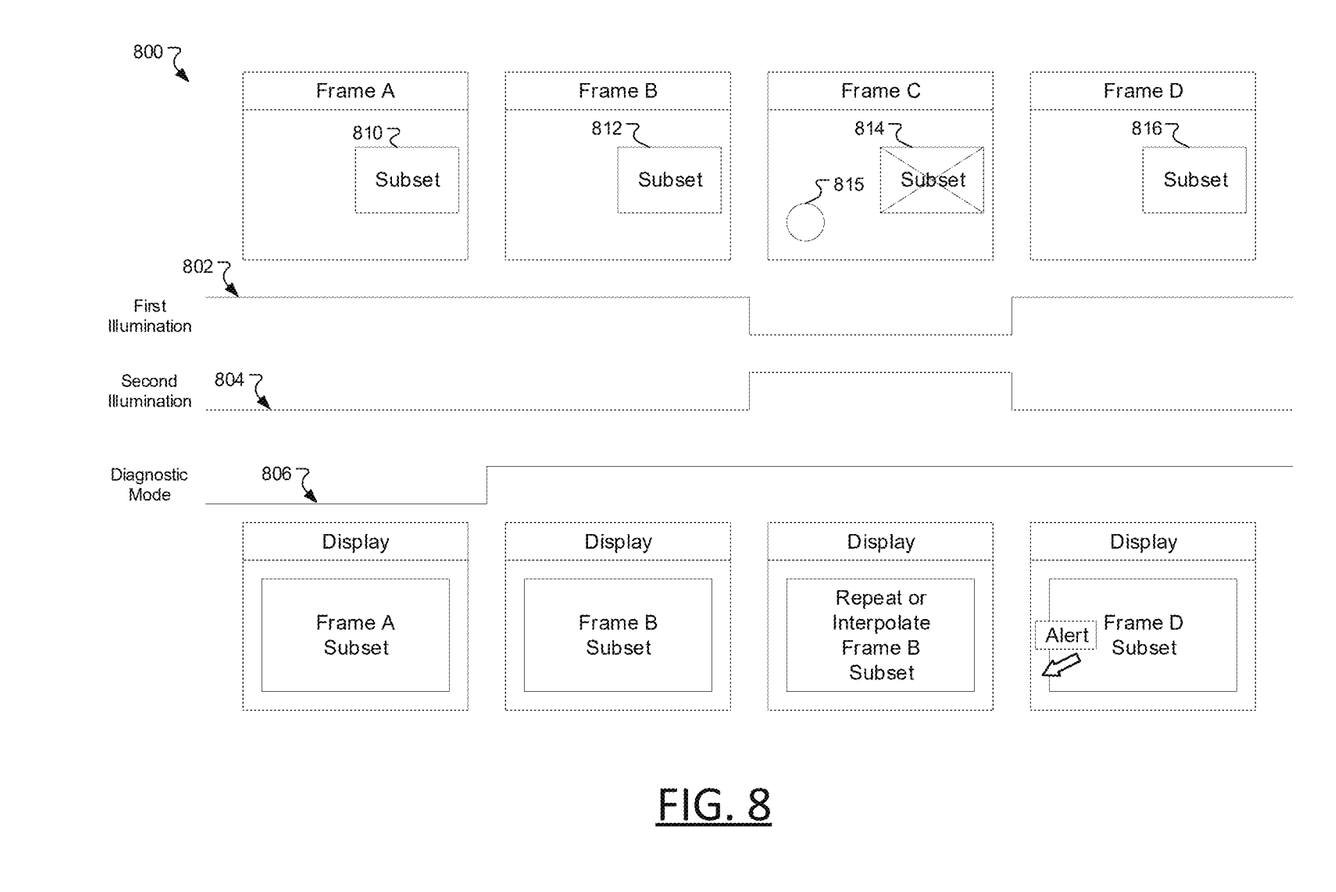
FIG. 8 shows a diagram 800 illustrating a process of changing imaging modes and creating display imagery according to an example embodiment.

FIG. 8 shows a diagram 800 illustrating a process of changing imaging modes and creating display imagery according to an example embodiment. The diagram is arranged as a time series from left to right. Depicted toward the top of diagram 800 is a series of acquired frames "Frame A", "Frame B", "Frame C", and "Frame D". Below this is shown a first illumination control signal 802 for the first imaging mode, a second illumination control signal 804 for the second imaging mode, and a diagnostic mode control signal 806. Toward the bottom of diagram 800 is depicted a series of displayed frames labeled "Display" which indicate the imaging data to be displayed during a series of frames displayed as a video on display 728.

During Frame A of the sequence, a subset of the Frame A image, ROI 810 is displayed the display. Frame A is captured in the first imaging mode, which in this embodiment includes the scope's light source emitting full visible spectrum light to produce a white light (WL) frame. The displayed image ROI 810 is a subset of Frame A at a position selected by the user.

The user activates the "background diagnostic" mode to alert when anomalies or FOIs are detected. In this embodiment, a diagnostic mode is provided in which the second imaging mode is enabled. The diagnostic mode is preferably switched on through a user interface element such as a button on the scope body or a software button in the user interface. The depicted Diagnostic Mode signal 806 illustrates the diagnostic mode being activated by a user before Frame B in the sequence, with the Diagnostic Mode signal going from a digital low value to a digital high value. At this point the scope is in the first imaging mode as shown by First Illumination signal 802 being high and Second Illumination signal 804 being low. Responsive to the diagnostic mode activation, the controller begins checking for the designated conditions to enter the second imaging mode.

In this embodiment, the designated conditions based upon which the processor changes to the second imaging mode are provided at a periodic cycle, which includes a designated number of frames captured in the first imaging mode and then at least one frame captured in the second imaging mode. For example, with a 30 frame-per-second video stream, the second imaging mode may be activated every 500 ms or 15 frames.

When the designated conditions are met, the first imaging mode is turned off and the second imaging mode is turned on, as indicated by First Illumination signal 802 going low and Second Illumination signal 804 going high between Frame B and Frame C. Preferably, Second Illumination signal 804 transitions to the on state after Frame B is formed, in a space between frames or overlapping a frame depending on blanking time between frames. One or more frames during transition may be discarded.

Depending on the type of illumination light used in the first and second states, Frame C is acquired second illumination state with either the second illumination light or both the first and second illumination lights. For example, if the second illumination state is fluorescent excitation light, the light source is changed to emit fluorescent illumination light and the visible light may be turned off. If the second illumination state includes illuminating with a brighter visible light or a wider area visible light, the light source of the first illumination state may be maintained and supplemented with additional light, by activating additional illumination ports or by increasing the power and brightness of the illumination ports in use. Either way, the visible light image of Frame C will be visibly different from the light used for Frame B and Frame D, and so Frame C is discarded for purposes of display to the user.

Acquiring the image data for the second imaging mode is preferably done with the same image sensor as that used for the first imaging mode. For embodiments in which fluorescent light is used for the second imaging mode, a dual mode sensor may be used, or a portion of the imaging light may be directed at a second sensor to acquire frames for the second imaging mode. For Frame C, the displayed image either repeats Frame B or interpolates a new image based at least partially on Frame B. In this scenario, the diagnostic image processing conducted on Frame C detects an anomaly or FOI (815).

After Frame C is acquired, the imaging mode is switched back to the first imaging mode by changing the illumination state using First Illumination signal 802 and Second Illumination signal 804. Then, Frame D is acquired using the first imaging mode.

The displayed image for Frame D includes an alert as depicted. It also includes an indicator showing the relative direction to FOI 815 detected in Frame C. This indicator may be used by the examining doctor or technician to decide to change their viewing area through the scope, either by moving the scope or adjusting the viewable area of the FOI.

While a series of Frames A, B, C, and D is shown, in some embodiments they are not consecutive frames, while in some they are. For example, if the diagnostic imaging processing requires more than a frame period of time to process Frame C, the alert may be added to a later frame of the first imaging mode. Further, a transition time between illumination states may cause more than one frame to be unsuitable for display before or after Frame C. In such case, repeated or interpolated data may be used for the display for those surrounding frames as well as Frame C.

While in this embodiment a periodic condition triggers the second imaging mode, in other embodiments other conditions are employed to trigger the second imaging mode. For example, some embodiments the designated conditions include receiving a signal from a movement sensor on the imaging scope indicating that the imaging scope has moved more than a designated threshold. This allows the diagnostic image processing to only be performed when a new region is viewed in the wide-angle view of the scope (the complete frame). In other embodiments, a similar affect is achieved by providing the designated conditions to be change in the content of the image frames in the ROI, or in the complete frame, above a designated threshold. In still other embodiments, a manual trigger may be provided for the user to activate the second imaging mode to capture one or more frames for diagnostic processing. Such a trigger may be embodied as a button on the scope or a software input element.

Figure 9:
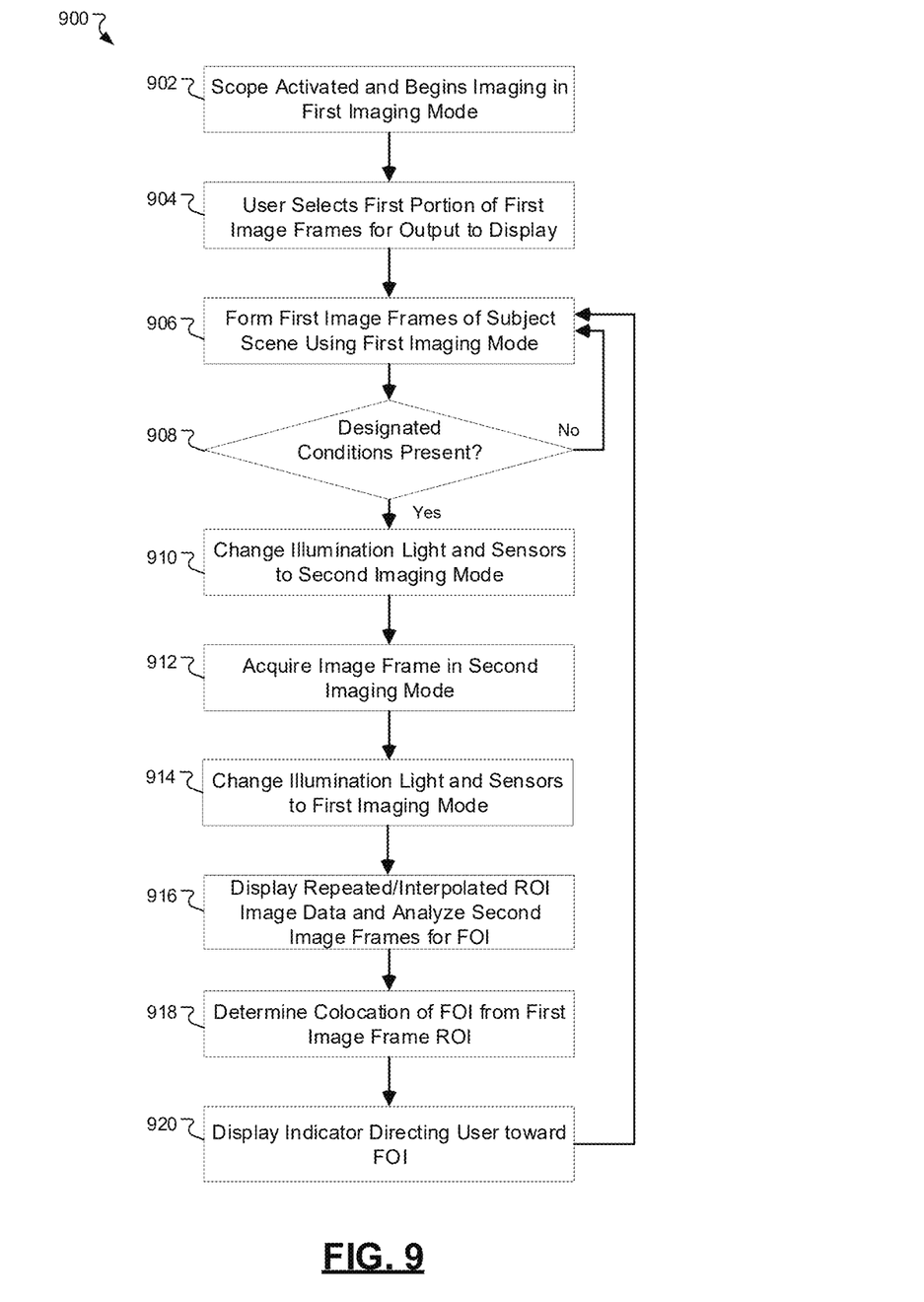
FIG. 9 shows a flowchart of a process for operating an imaging scope system according to some embodiments.

FIG. 9 shows a flowchart 900 of a process for operating an imaging scope system according to some embodiments.

The depicted process is suitable for use with the imaging scope system described above and variations thereof.

The process starts at block 902 where the scope is activated and begins imaging in the first imaging mode. A user selects a first portion of the available wide angle display area to output to the display as the ROI at block 904. As shown at blocks 906 and 908, the process continues forming image frames and displaying an ROI using the first imaging mode until designated conditions are present at block 908. The display presents the frames as a video view on the display such as display 728 (FIG. 7).

Responsive to designated conditions, such as the completion of a designated periodic time or a movement as described above, the process at block 910 changes the system to use the second imaging mode by adjusting the illumination light emitters and sensors accordingly. A frame is then acquired in the second imaging mode at block 912.

Next at block 914 the process changes the imaging mode back to the first imaging mode by adjusting the illumination light emitters and sensors accordingly. Preferably as soon as a second imaging mode frame is received at the controller, diagnostic image processing is used to analyze the second imaging mode frame for the presence of one or more FOI at block 916. A repeated or interpolated frame is also inserted into the video display stream at block 916 to replace the frame acquired in the second imaging mode.

If an FOI is detected in the analysis, at block 918 the process determines a collocation or relative direction on the display from the currently set display area for the ROI to the detected FOI in the second imaging frame. This direction is displayed as an indicator directing the user toward the FOI. The indicator preferably is generated as soon as the results of the analysis at block 916 are ready. The process may further track movement of the ROI (by moving the scope or adjusting the ROI portion of the frame) after the indicator is presented and remove the indicator or provide a second indicator to tell the practitioner when the displayed ROI includes the area of the detected FOI.

For embodiments that employ FI detection for the second imaging mode, the analysis and indicator features have the benefit of identifying to medical practitioners where anomalous features are such as potential colon cancers and potential bladder cancers.

Figure 10:
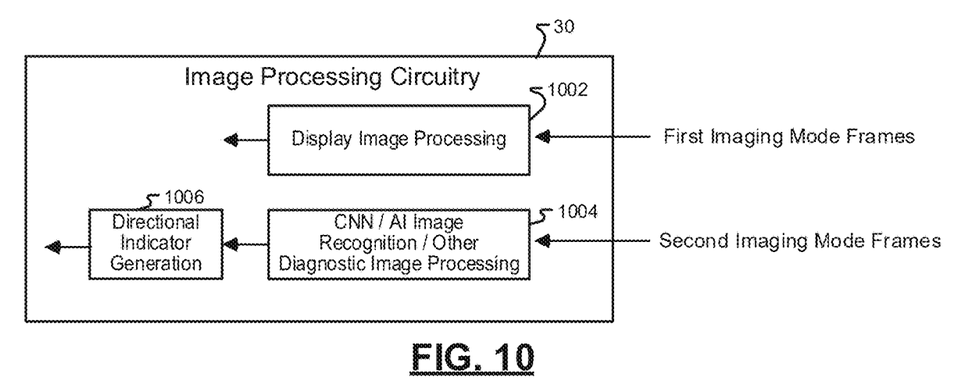
FIG. 10 shows in block diagram form a portion of image processing circuitry according to some embodiments.

FIG. 10 shows in block diagram form a portion of image processing circuitry 30 according to some embodiments. Image data from the first imaging mode frames is fed to display image processing 1002 circuitry which prepares the data for display. In parallel, the second image mode frames are fed to diagnostic image processing circuitry such as a convolutional neural network circuit, an artificial intelligence feature recognition circuit, or another suitable diagnostic image processing circuit. Any of a variety of known artificial intelligence (AI) algorithm for detecting features of interest such as cancerous or precancerous tumors or lesions may be used. For example, in one embodiment the AI algorithm includes a convolutional neural network (CNN) trained for recognizing features in the image data. While separate, parallel circuitry is shown in these embodiments, the functionality may instead be implemented in DSP programming running on the same processing core or separate cores. Programmable logic or other suitable known techniques may also be used to implement image processing circuitry 30 in various embodiments.

When FOI are detected, data describing the detected features location is fed to directional indicator generation circuitry 1006, which calculates the relative direction of the FOI from the currently displayed ROI and generates commands to display an appropriate directional indicator or alert as described above.

Figure 11:
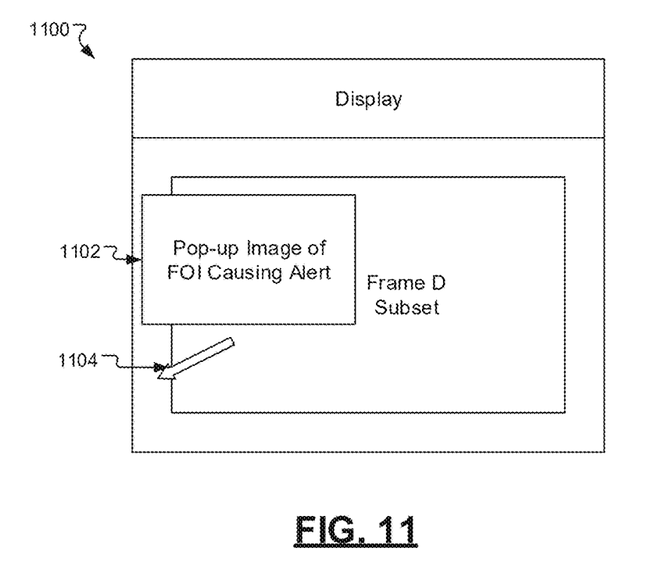
FIG. 11 shows a diagram depicting a display output according to some embodiments.

FIG. 11 shows a diagram 1100 illustrating an alternative alert display process according to some additional embodiments. The depicted alert display 1100 is suitable for use to display an alert such as the alert depicted in FIG. 8, Frame D. In this implementation, while the background diagnostic mode described with respect to FIG. 8 is active, in addition to the alert arrow 1104 indicating a relative direction to an FOI, the process also responds to detection of an FOI by displaying a pop-up image 1102 of the FOI causing the alert. Image 1102 preferably displays data acquired in the second imaging mode (for example, data acquired in Frame C of FIG. 8), giving the user an indication of what caused an FOI to be identified by the image processing algorithm. In some embodiments, image 1102 may be displayed with image data acquired in the first imaging mode. Although this distribution of imaging device functional control among multiple programmable logic devices, processors, and controllers is typical, these programmable logic devices, processors, or controllers can be combinable in various ways without affecting the functional operation of the imaging device and the application of the invention. These programmable logic devices, processors, or controllers can comprise one or more programmable logic devices, digital signal processor devices, microcontrollers, or other digital logic circuits. Although a combination of such programmable logic devices, processors, or controllers has been described, it should be apparent that one programmable logic device, digital signal processor, microcontroller, or other digital logic circuit can be designated to perform all of the needed functions. All of these variations can perform the same function and fall within the scope of this invention.

As used herein the terms "comprising," "including," "carrying," "having" "containing," "involving," and the like are to be understood to be open-ended, that is, to mean including but not limited to. Any use of ordinal terms such as "first," "second," "third," etc., in the claims to modify a claim element does not by itself connote any priority, precedence, or order of one claim element over another, or the temporal order in which acts of a method are performed. Rather, unless specifically stated otherwise, such ordinal terms are used merely as labels to distinguish one claim element having a certain name from another element having a same name (but for use of the ordinal term).

The foregoing has outlined rather broadly the features and technical advantages of the invention in order that the detailed description of the invention that follows may be better understood. It should be appreciated by those skilled in the art that the conception and specific embodiments disclosed may be readily utilized as a basis for modifying or designing other structures for carrying out the same purposes of the invention. It should also be realized by those skilled in the art that such equivalent constructions do not depart from the scope of the invention as set forth in the appended claims.

Although the invention and its advantages have been described in detail, it should be understood that various changes, substitutions and alterations can be made herein without departing from the scope of the invention as defined by the appended claims. The combinations of features described herein should not be interpreted to be limiting, and the features herein may be used in any working combination or sub-combination according to the invention. This description should therefore be interpreted as providing written support, under U.S. patent law and any relevant foreign patent laws, for any working combination or some subcombination of the features herein.

Moreover, the scope of the present application is not intended to be limited to the particular embodiments of the process, machine, manufacture, composition of matter, means, methods and steps described in the specification. As one of ordinary skill in the art will readily appreciate from the disclosure of the invention, processes, machines, manufacture, compositions of matter, means, methods, or steps, presently existing or later to be developed that perform substantially the same function or achieve substantially the same result as the corresponding embodiments described herein may be utilized according to the invention. Accordingly, the appended claims are intended to include within their scope such processes, machines, manufacture, compositions of matter, means, methods, or steps.

The invention claimed is:

1. An imaging scope system, comprising:
    a shaft including a distal tip with a light emitter providing illumination light and an optical assembly including a wide-angle lens element;
    an image sensor assembly including an image sensor configured to receive at least a portion of light focused through the optical assembly and produce output signals;
    image forming circuitry adapted to receive the output signals and produce an image signal communicating a series of image frames;
    a processor coupled to the image forming circuitry and configured to:
        condition the image signal for presentation on an electronic display, the presentation including an adjustable region of interest (ROI) smaller than a field of view of the image sensor;
        responsive to designated conditions, capture a frame from a series of image frames, by the image sensor, for diagnostic image processing, and evaluate results of the diagnostic image processing to determine whether a feature of interest (FOI) is present in the frame, wherein, during a time in which the frame is captured, causing the light emitter on the imaging scope to alter illumination light from a first state to a second state, and return to the first state following the capture of the frame; and
        responsive to an FOI being present in the frame but outside the ROI, create a notification on the electronic display.

2. The system according to claim 1, wherein spectral content of the second state is different than the spectral content of first state.

3. The system according to claim 2, wherein the second state comprises illumination light appropriate to stimulate fluorescence in prepared tissue.

4. The system according to claim 3, wherein the second state consists substantially of light from a spectral band spanning 350-450 nm.

5. The system according to claim 1, wherein second state is of a higher intensity than the first state.

6. The system according to claim 1, wherein the second state has a wider field of illumination than that of the first state.

7. The system according to claim 1, wherein the processor is further configured to:
    cause the selected frame not to be displayed in the presentation, and instead replacing the selected frame with imagery based on at least one frame prior to the selected frame.

8. The system according to claim 1, wherein the notification indicates a relative direction from the ROI to the FOI.

9. The system according to claim 1, wherein the diagnostic image processing comprises an artificial intelligence (AI) algorithm configured to detect cancerous or precancerous tumors or lesions.

10. The system according to claim 9, wherein the AI algorithm comprises a trained convolutional neural network (CNN).

11. The system according to claim 1, wherein the designated conditions include waiting at least 500 ms for a next image acquisition.

12. The system according to claim 1, wherein the designated conditions include receiving a signal from a movement sensor on the imaging scope indicating that the imaging scope has moved more than a designated threshold.

13. The system according to claim 1, wherein the designated conditions include a change in content of the series of image frames in the ROI above a predetermined threshold.

14. A method comprising:
    receiving, at a processor, an image signal based on sensor data received from an image sensor of an imaging scope;
    conditioning the image signal for presentation on an electronic display, the presentation including an adjustable region of interest (ROI) smaller than a field of view of the image sensor;
    responsive to designated conditions, capturing a frame from a series of image frames, by the image sensor, for diagnostic image processing, wherein, during a time in which the frame is captured, causing a light emitter on the imaging scope to alter illumination light from a first state to a second state, and return to the first state following the capture of the frame;
    performing the diagnostic image processing and evaluating results of the diagnostic image processing to determine whether a feature of interest (FOI) is present in the selected frame; and
    responsive to the FOI being present in the selected frame but outside of the ROI, causing a notification to be displayed on the electronic display.

15. The method according to claim 14, wherein spectral content of the second state is different than the spectral content of first state.

16. The method according to claim 15, wherein the second state comprises illumination light appropriate to stimulate fluorescence in prepared tissue.

17. The method according to 16, wherein the second state consists substantially of light from a spectral band spanning 350-450 nm.

18. The method according to claim 14, wherein the second state is of a higher intensity than the first state.

19. The method according to claim 14, wherein the second state has a wider field of illumination than that of the first state.

20. The method according to claim 14, further comprising causing the selected frame not to be displayed in the presentation, and instead replacing the selected frame with imagery based on at least one frame prior to the selected frame.

21. The method according to claim 14, wherein the notification indicates a relative direction from the ROI to the FOI.

22. The method according to claim 14, wherein the diagnostic image processing comprises an artificial intelligence (AI) algorithm configured to detect cancerous or precancerous tumors or lesions.

23. The method according to claim 22, wherein the AI algorithm comprises a trained convolutional neural network (CNN).

24. The method according to claim 14, wherein the designated conditions include waiting at least 500 ms for a next image acquisition.

25. The method according to claim 14, wherein the designated conditions include receiving a signal from a movement sensor on the imaging scope indicating that the imaging scope has moved more than a designated threshold.

26. The method according to claim 14, wherein the designated conditions include a change in content of the series of image frames in the ROI above a predetermined threshold.

* * * * *